US009101575B2

(12) United States Patent
Hla et al.

(10) Patent No.: US 9,101,575 B2
(45) Date of Patent: Aug. 11, 2015

(54) METHODS OF INHIBITING VASCULAR PERMEABILITY AND APOPTOSIS

(75) Inventors: Timothy Hla, Avon, CT (US); Teresa Sanchez, West Hartford, CT (US); Kevin Patrick Claffey, Burlington, CT (US); Ji-Hye Paik, New Britain, CT (US)

(73) Assignee: THE UNIVERSITY OF CONNECTICUT, Farmington, CT (US)

( * ) Notice: Subject to any disclaimer, the term of this patent is extended or adjusted under 35 U.S.C. 154(b) by 192 days.

(21) Appl. No.: 12/894,783

(22) Filed: Sep. 30, 2010

(65) Prior Publication Data

US 2011/0015159 A1 Jan. 20, 2011

Related U.S. Application Data

(62) Division of application No. 10/562,305, filed as application No. PCT/US2004/019420 on Jun. 18, 2004, now Pat. No. 7,838,562.

(60) Provisional application No. 60/482,234, filed on Jun. 24, 2003.

(51) Int. Cl.
*A61K 31/133* (2006.01)
*A61K 31/137* (2006.01)
*A61K 31/00* (2006.01)
A61K 31/661 (2006.01)

(52) U.S. Cl.
CPC ............. *A61K 31/133* (2013.01); *A61K 31/00* (2013.01); *A61K 31/137* (2013.01); *A61K 31/661* (2013.01)

(58) Field of Classification Search
CPC .................................................. A61K 31/137
USPC ......................................................... 514/653
See application file for complete search history.

(56) References Cited

U.S. PATENT DOCUMENTS

| | | | |
|---|---|---|---|
| 5,948,820 A | 9/1999 | Fujita et al. | |
| 6,004,565 A | 12/1999 | Chiba et al. | |
| 6,187,756 B1 * | 2/2001 | Lee et al. | 514/26 |
| 6,187,821 B1 | 2/2001 | Fujita et al. | |
| 6,274,629 B1 | 8/2001 | Cottens et al. | |
| 6,372,800 B1 | 4/2002 | Fujita et al. | |
| 6,471,980 B2 | 10/2002 | Sirhan et al. | |
| 6,476,004 B1 | 11/2002 | Sakai et al. | |
| 6,486,209 B2 | 11/2002 | Cottens et al. | |
| 2001/0056124 A1 | 12/2001 | Cottens et al. | |
| 2002/0169159 A1 * | 11/2002 | Medina et al. | 514/227.5 |
| 2003/0082743 A1 | 5/2003 | Bergsma et al. | |
| 2004/0058894 A1 | 3/2004 | Doherty et al. | |

FOREIGN PATENT DOCUMENTS

| | | | |
|---|---|---|---|
| WO | 03061567 A2 | 7/2003 | |
| WO | 2004010987 A2 | 2/2004 | |

OTHER PUBLICATIONS

McGeer et al., Innate Inflammatory Reaction of the Brain in Alzheimer Disease, 1997, McGill Journal of Medicine, vol. 3, No. 2, pp. 134-141.*
Chiba et al., FTY720, a Novel Immunosuppressant, Induces Sequestration of Circulating Mature Lymphocytes by Acceleration of Lymophocyte Homing in Rats. I. FTY720 Selectively Decreases the Number of Circulating Mature Lymphocytes by Acceleration of Lymphocyte Homing, 1998, Journal of Immunology, vol. 160, pp. 5037-5044.*
Mandela, S., Hajdu, R., Bergstrom, J., Quackenbush, E., Xie, J., Milligan, J., Thornton, R., Shei, G.J., Card, D., Keohane, C., et al. 2002. Alteration of lymphocyte trafficking by sphingosine-1-phosphate receptor agonists. Science 296:346-349.
Brinkmann, V., Davis, M.D., Heise, C.E., Albert, R., Cottens, S., Hof, R., Bruns, C., Prieschl, E., Baumruker, T., Hiestand, P., et al. 2002. The immune modulator FTY720 targets sphingosine 1-phosphate receptors. J Biol Chem 277:21453-21457.
Biedermann, B.C., Sahner, S., Gregor, M., Tsakiris, D.A., Jeanneret, C., Pober, J.S., and Gratwohl, A. 2002. Endothelial injury mediated by cytotoxic T lymphocytes and loss of microvessels in chronic graft versus host disease. Lancet 359:2078-2083.
Corada, M., Mariotti, M., Thurston, G., Smith, K., Kunkel, R., Brockhaus, M., Lampugnani, M.G., Martin-Padura, I., Stoppacciaro, A., Ruco, L., et al. 1999. Vascular endothelial-cadherin is an important determinant of microvascular integrity in vivo. Proc Natl Acad Sci U S A 96:9815-9820.
Hordijk, P.L., Anthony, E., Mul, F.P., Rientsma, R., Oomen, L.C., and Roos, D. 1999. Vascular-endothelial-cadherin modulates endothelial monolayer permeability. J Cell Sci 112 ( Pt 12)1915-1923.
Garcia, J.G., Liu, F., Verin, A.D., Birukova, A., Dechert, M.A., Gerthoffer, W.T., Bamberg, J.R., and English, D. 2001. Sphingosine 1-phosphate promotes endothelial cell barrier integrity by Edg-dependent cytoskeletal rearrangement. J Clin Invest 108:689-701.
Hotchkiss, R.S., Tinsley, K.W., Swanson, P.E., and Karl, I.E. 2002. Endothelial cell apoptosis in sepsis. Crit Care Med 30:S225-228.
Lei, H.Y., Yeh, T.M., Liu, H.S., Lin, Y.S., Chen, S.H., and Liu, C.C. 2001. Immunopathogenesis of dengue virus infection. J Biomed Sci 8:377-388.

(Continued)

*Primary Examiner* — James D Anderson
*Assistant Examiner* — Meghan Finn
(74) *Attorney, Agent, or Firm* — Cantor Colburn LLP

(57) ABSTRACT

Agonists of vascular endothelial sphingosine-1-phosphate receptors are described. Compounds such as FTY720 can be phosphorylated by sphingosine kinase-2 into the phosphorylated forms which serve as sphingosine-1-phosphate receptor agonists. The vascular endothelial sphingosine-1-phosphate receptor agonists are employed in methods of treating a mammal for vascular permeability disorders and unwanted vascular endothelial cell apoptosis, and for the growth of new blood vessels. The sphingosine-1-phosphate receptor agonists can be used for the manufacture of a medicament for treating vascular permeability disorders and unwanted vascular endothelial cell apoptosis, and for the growth of new blood vessels.

1 Claim, 8 Drawing Sheets

(56) References Cited

OTHER PUBLICATIONS

Avirutnan, P., Malasit, P., Seliger, B., Bhakdi, S., and Husmann, M. 1998. Dengue virus infection of human endothelial cells leads to chemokine production, complement activation, and apoptosis. J Immunol 161:6338-6346.

Garcia, J.G., Siflinger-Birnboim, A., Bizios, R., Del Vecchio, P.J., Fenton, J.W., 2nd. and Malik, A.B. 1986. Thrombin-induced increase in albumin permeability across the endothelium. J Cell Physiol 128:96-104.

Rafi-Janajreh, A.Q., Chen, D., Schmits, R., Mak, T.W., Grayson, R.L., Sponenberg, D.P., Nagarkatti, M., and Nagarkatti, P.S. 1999. Evdence for the involvement of CD44 in endohelial cell injury and induction of vascular leak syndrome by IL-2. J Immunol 163:1619-1627.

McMillan, D.E. 1984. The microcirculation in diabetes. Microcirc Endothelium Lymphatics 1:3-24.

Publication No. EP 1 643 983 ; Application No. 04 776 717.3-2123; Office Action dated Mar. 9, 2007; 2 pages.

International Search Report and Written Opinion; International Application No. PCT/US2004/019420; International Filing Date: Jun. 18, 2004; Date of Mailing Mar. 10, 2005; 10 pages.

Udobi, et al.; "Acute Respiratory Distress Syndrome"; American Family Physician; 67(2); pp. 315-322; (2003).

Bates et al.; "Regulation of Microvascular Permeability by Vascular Endothelial Growth Factors"; J. Anat. 200; pp. 581-597; (2002).

Sanchez, et al.; "Phosphorylation and Action of the Immunomodulator FTY720 Inhibits Vascular Endothelial Cell Growth Factor-induced Vascular Permeability"; the Journal of Biological Chemistry; 278; No. 47; pp. 47281-47290; (2003).

Dudek, et al.; "Cytoskeletal Regulation of Pulmonary Vascular Permeability"; J. Appl. Physiol.; 91; pp. 1487-1500; (2001).

Mortelliti, et al.; "Acute Respiratory Distress Syndrome"; American Family Physician; 65; pp. 1823-1830; (2002).

Ishi, Yoshiki; "Vascular Endothelial Cell"; Journal of Clinical and Experimental Medicine; vol. 170; No. 1; English Translation ; (1994).

Lee et al.; "Vascular Endothelial Cell Adherens Junction Assembly and Morphogenesis Induced by Sphingosine-1-Phosphate"; Cell; 99; pp. 301-312; (1999).

Brinkmann et al.; "The Immune Modulator FTY720 Targets Sphingosine 1-Phosphate Receptors"; The Journal of Biological Chemistry; 227(24); pp. 21453-21457; (2002).

Hwang et al.; "FTY720, a new Immunosuppressant, Promotes Long-Term Graft Survival and Inhibits the Progression of Graft Coronary Artery Disease in a Murine Model of Cardiac Tansplantation"; Circulation; 100(12); pp. 1322-1329; (1999).

Maceyka et al.; "Sphingosine Kinase, Sphingosine-1-Phosphate, and Apoptosis"; Biochimica et Biophysica Acta; 1585; pp. 193-201 (2002).

Schaphorst et al.; "Role of Sphingosine-1 Phosphate in the Enhancement of Endothelial Barrier Integrity by Platelet-Released Products"; Am J Phsiol Lung Cell Mol Physiol; 285; pp. L258-L267; (2003).

Yang et al.; "The Immune Modulator FYT720 Prevents Autoimmune Diabetes in Nonobese Diabetic Mice"; Clinical Immunology; 107; pp. 30-35; (2003).

Low-dose Prednisone Found Ineffective Against Alzheimer's Disease; Researchers Continue to Look at NSAIDs, Other Drugs; NIA Press Office; National Institute on Aging; Feb. 7, 2000. http://www.nia.nih.gov/newsroom/2000/02/low-dose-prednisone-found-ineffective-again.

Aisen et al.; "A Randomized Controlled Trial of Prednisone in Alzheimer's Disease. Alzheimer's Disease Cooperative Study"; Neurology; 54(3); p. 588-593; 2000, Abstract only.

Kovarik et al.; "Expert Opinion on Emerging Drugs"; Informa; 8(1); pp. 47-62;2003; Abstract only.

Adachi et al. "FTY720 Story. Its Discovery and the Following Accelerated Development of Sphingosine 1-Phosphate Receptor Agonists as Immunomodulators Based on Reverse Pharmacology"; Perspectives in Medicinal Chemistry; pp. 11-23; (2007).

Asle-Rousta et al.; "FTY720 (fingolimod) Attenuates Beta-Amyloid Peptide (AB42)-Induced Impairment of Spatial Learning and Memory in Rats"; J Mol Neurosci; 50(3); pp. 524-532; Abstract Only (2013).

Hemmati et al.; "Neurorestorative Effect of FTY720 in a Rat Model of Alzheimer's Disease: Comparison with Memantine"; Behav Brain Res; 252; pp. 415-421; Abstract only; (2013).

* cited by examiner

S1P(100nM)
FTY-P(10nM)
(R)-AFD(10nM)
PTx (200ng/mL)

C   S1P

FTY   FTY-I

AAL   AFD

SEQUENCE LISTING

```
<160> NUMBER OF SEQ ID NOS: 4

<210> SEQ ID NO 1
<211> LENGTH: 20
<212> TYPE: DNA
<213> ORGANISM: Mus musculus

<400> SEQUENCE: 1
tggagtatga atgcccctac                                               20

<210> SEQ ID NO 2
<211> LENGTH: 19
<212> TYPE: DNA
<213> ORGANISM: Mus musculus

<400> SEQUENCE: 2
cgctaaccat caattcccc                                                19

<210> SEQ ID NO 3
<211> LENGTH: 20
<212> TYPE: DNA
<213> ORGANISM: Mus musculus

<400> SEQUENCE: 3
gatcacccct gacctgctac                                               20

<210> SEQ ID NO 4
<211> LENGTH: 20
<212> TYPE: DNA
<213> ORGANISM: Mus musculus

<400> SEQUENCE: 4
ggcatcttca cagcttcctc                                               20
```

METHODS OF INHIBITING VASCULAR PERMEABILITY AND APOPTOSIS

CROSS REFERENCE TO RELATED APPLICATIONS

This application is a divisional of U.S. application Ser. No. 10/562,305 filed Mar. 9, 2007, which is a 371 of PCT/US04/19420 filed Jun. 18, 2004, which claims priority from Provisional Application Ser No. 60/482,234, filed Jun. 24, 2003, which are incorporated herein by reference in their entirety.

STATEMENT REGARDING FEDERALLY SPONSORED RESEARCH & DEVELOPMENT

The U.S. Government has certain rights in this invention pursuant to Grant Nos. HL67330 and HL70694 awarded by the National Institute of Health.

BACKGROUND

The process of forming new blood vessels is termed angiogenesis. During angiogenesis, vascular endothelial cells undergo orderly proliferation, migration, and morphogenesis to form new capillary networks. Under normal or non-pathologic conditions, angiogenesis occurs under well-defined conditions such as in wound healing, in response to ischemia, and during embryonal and fetal development. However, persistent or uncontrolled angiogenesis can lead to a variety of disease states or conditions and, in the case of solid tumors, may be a necessary condition to maintain the disease state.

Many extracellular and intracellular signaling molecules interact with cellular receptors and regulate effects in the vascular system, including processes related to angiogenesis. Sphingosine-1-phosphate (S1P) is a bioactive sphingolipid that mediates a wide variety of cellular responses through interaction with the members of the endothelial cell differentiation gene family (EDG also known as $S1P_n$ receptors) of plasma membrane-localized G protein-coupled receptors. To date, five members of this family have been identified as S1P receptors in different cell types, $S1P_1$/EDG-1, $S1P_2$/EDG-5, $S1P_3$/EDG-3, $S1P_4$/EDG-6 and $S1P_5$/EDG-8. In particular, S1P interaction with the $S1P_1$ and $S1P_3$ receptors has been demonstrated to play an important role in survival and morphogenesis of endothelial cells in vitro and $S1P_1$ is necessary for vascular maturation in vivo. However, S1P also exerts potent effects on other organ systems, such as the immune system and the reproductive system, indicating that it is a multifunctional lipid mediator.

S1P and its receptors are involved in the regulation of vasculature. It is thus desirable to manipulate S1P receptors, particularly in the treatment of diseases of the vascular system.

BRIEF SUMMARY

A method of treating a mammal in need of treatment for a vascular permeability disorder comprises administering to the mammal an effective amount of a vascular endothelial sphingosine-1-phosphate receptor agonist, wherein the vascular endothelial sphingosine-1-phosphate receptor agonist is not sphingosine-1-phosphate.

A method of treating a mammal in need of treatment for unwanted vascular endothelial cell apoptosis comprises administering to the mammal an effective amount of a vascular endothelial sphingosine-1-phosphate receptor agonist, wherein the vascular endothelial sphingosine-1-phosphate receptor agonist is not sphingosine-1-phosphate, and wherein the unwanted vascular endothelial cell apoptosis is not related to transplant rejection.

A method of stimulating new blood vessel formation in a mammal comprises administering to a site in the mammal an effective amount of a vascular endothelial sphingosine-1-phosphate receptor agonist, wherein the vascular endothelial sphingosine-1-phosphate receptor agonist is not sphingosine-1-phosphate.

In one embodiment, disclosed is the use of a vascular endothelial sphingosine-1-phosphate receptor agonist, a pharmaceutically acceptable form thereof, or a phosphorylated form thereof, for the manufacture of a medicament for the treatment of a vascular permeability disorder, wherein the vascular endothelial sphingosine-1-phosphate receptor agonist is not sphingosine-1-phosphate.

In another embodiment, disclosed is the use of a vascular endothelial sphingosine-1-phosphate receptor agonist, a pharmaceutically acceptable form thereof, or a phosphorylated form thereof, for the manufacture of a medicament for the treatment of unwanted vascular endothelial cell apoptosis, wherein the vascular endothelial sphingosine-1-phosphate receptor agonist is not sphingosine-1-phosphate, and wherein the unwanted vascular endothelial cell apoptosis is not related to transplant rejection.

In yet another embodiment, disclosed is the use of a vascular endothelial sphingosine-1-phosphate receptor agonist, a pharmaceutically acceptable form thereof, or a phosphorylated form thereof, for the manufacture of a medicament for the stimulation of new blood vessel formation in a mammal, wherein the vascular endothelial sphingosine-1-phosphate receptor agonist is not sphingosine-1-phosphate.

BRIEF DESCRIPTION OF THE DRAWINGS

Referring now to the drawings wherein like elements are numbered alike in several FIGURES.

DETAILED DESCRIPTION

Figure 1:
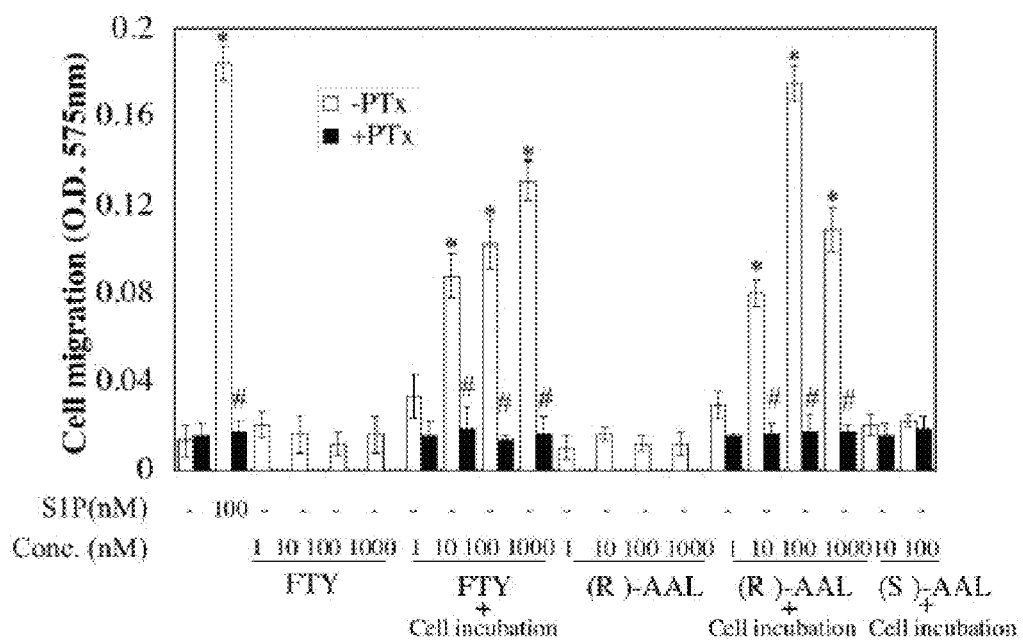
FIG. 1 is a graph of the results of a cell migration test for HUVECs exposed to FTY720 and (R)-AAL with and without cell incubation.

FTY720 is a potent immunomodulator that has shown effects in animal models of organ transplantation as shown in U.S. Pat. Nos. 6,486,209; 6,476,004; 6,471,980; 6,372,800; 6,274,629; 6,187,821; 6,004,565; and 5,948,820 which are incorporated herein by reference. The mechanism of action of this compound was recently shown to include phosphorylation into FTY720-P, which is an agonist for four of five S1P receptors in T lymphocytes. It was shown previously that FTY720 is a potent modulator of lymphocyte trafficking, however, the effect of FTY720 on vascular elements was previously unknown.

It is demonstrated herein that vascular endothelial cells contain enzyme systems to "activate" FTY720 and its analogs. Cultured endothelial cells such as human umbilical vein endothelial cells (HUVEC) are accepted in vitro model systems for studying angiogenesis. Upon incubation with HUVEC conditioned medium or cell extracts, FTY720 is phosphorylated and is able to activate the endothelial cells to migrate in a pertussis toxin sensitive manner, suggesting that it is activating the $G_i$-coupled S1P receptors. It is shown herein that endothelial cell-derived sphingosine kinase-2 (SK2) is involved in metabolism of FTY720 into FTY720-P.

It is also shown herein that FTY720-P and its analog (R)-AFD activate vascular S1P receptors and stimulate signaling pathways in a manner similar to S1P. These events result in the inhibition of endothelial cell apoptosis, which occurs in various pathological conditions in which vascular system is stressed. Another physiologically relevant effect of S1P receptor agonists is the induction of adherens junction assembly in endothelial cells. It is also shown that VE-cadherin translocation is induced after S1P, FTY720-P and (R)-AFD stimulation. The cell-cell junction molecules are an important target of mediators that regulate vascular permeability. S1P, FTY720-P and (R)-AFD can block VEGF-induced paracellular permeability in vitro and VEGF-induced vascular permeability in vivo. The induction of adherens junction assembly in endothelial cells by FTY720-P and (R)-AFD may have two important applications in vivo. On one hand, it may be a part of the mechanism of action of FTY720. FTY720 could prevent egression of lymphocytes into the lymphatic sinus by regulating cell-cell junctions at the sinus-lining endothelium. In fact, FTY720-P inhibits chemokine-induced migration of T lymphocytes through an endothelial cell monolayer in vitro. On the other hand, FTY720 may be able to inhibit vascular permeability in acute vasculopathic situations, such as respiratory distress syndrome which occurs as a complication of sepsis. In addition, long term changes in vascular permeability is a hallmark of endothelial cell injury and may lead to chronic diseases common to ischemic cardiovascular disease and peripheral vascular disorders associated with diabetes. FTY720-P is a potent modifier of the vascular system and that it may be used as a protector of the endothelial cell integrity in situations where it is compromised.

The present invention thus relates to methods of treating a mammal in need of treatment for a vascular permeability disorder, to methods of inhibiting vascular endothelial cell apoptosis, and to methods of stimulating new blood vessel formation. The methods comprise administering to the mammal an effective amount of an agonist of a vascular endothelial S1P receptor, other than S1P itself. The agonists of vascular endothelial S1P receptors, or a pharmaceutically acceptable form thereof, may be used for the manufacture of a medicament for the treatment of a disease, disorder, or state responsive to an agonist of a vascular endothelial S1P receptor. Suitable vascular endothelial S1P receptors include, for example, $S1P_1$, $S1P_2$, $S1P_3$, $S1P_4$, $S1P_5$, and combinations comprising one or more of the foregoing receptors. In one embodiment, S1P receptors include $S1P_1$, $S1P_3$, and combinations thereof. The agonist of a vascular endothelial S1P receptor may be a pharmaceutically acceptable salt and/or be phosphorylated by a sphingosine-kinase 2 enzyme.

Suitable agonists of vascular endothelial S1P receptors include, for example, 1,2 aminoalcohols, the pharmaceutically acceptable salts thereof, the phosphorylated forms thereof, and combinations comprising one or more of the foregoing agonists.

"Pharmaceutically acceptable forms" of the agonists of vascular endothelial S1P receptors recited herein include pharmaceutically acceptable salts, hydrates, solvates, crystal forms, polymorphs, chelates, non-covalent complexes, esters, clathrates, prodrugs, and mixtures of such compounds. Pharmaceutically acceptable salts are a suitable pharmaceutically acceptable form.

"Pharmaceutically acceptable salts" include derivatives of the agonists of vascular endothelial S1P receptors wherein the parent compound is modified by making non-toxic acid or base salts thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. The pharmaceutically acceptable salts can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts may be found, e.g., in *Remington's Pharmaceutical Sciences*, 17th ed., Mack Publishing Company, Easton, Pa., p. 1418 (1985).

Suitable 1,2-aminoalcohols have the formula

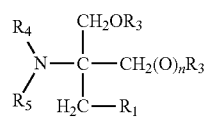

(I)

wherein $R_1$ is a substituted or unsubstituted, straight or branched carbon chain having 12 to 22 carbon atoms which may be optionally interrupted by a substituted or unsubstituted phenylene or phenoxy; each of $R_2$, $R_3$, $R_4$ and $R_5$, independently, is hydrogen or $C_{1-6}$ alkyl; and n is 0 or 1. In one embodiment, compounds of formula I are those wherein $R_1$ is a straight or branched chain alkyl having 13 to 20 carbon atoms, optionally substituted by nitro, halogen, amino, hydroxy or carboxylic acid, and, more preferably those wherein $R_1$ is (phenyl)alkyl- wherein the phenyl is substituted by a straight or branched $C_{6-14}$ alkyl or $C_{6-14}$ alkoxy chain optionally substituted by halogen and the alkyl moiety is a $C_{1-6}$ alkyl optionally substituted by hydroxy. In one embodiment, $R_1$ is (phenyl) $C_{1-6}$ alkyl-substituted on the phenyl by a straight or branched $C_{6-14}$ alkyl or $C_{6-14}$ alkoxy chain. The $C_{6-14}$ alkyl chain may be in ortho, meta or para-position. In one embodiment, each of $R_2$ to $R_5$ is hydrogen.

As used herein, optionally interrupted means that an alkyl chain can be interposed at any point within the alkyl chain. See, for example, formula 2. A dash ("-") that is not between two letters or symbols is used to indicate a point of attachment for a substituent. For example, (phenyl)alkyl-is attached through the carbon atom of the alkyl group.

As used herein, "alkyl" is intended to include both branched and straight-chain saturated aliphatic hydrocarbon groups, having the specified number of carbon atoms. Thus, the term $C_1$-$C_6$ alkyl as used herein includes alkyl groups having from 1 to 6 carbon atoms. When $C_0$-$C_n$ alkyl is used herein in conjunction with another group, for example, (phenyl)$C_0$-$C_4$ alkyl, the indicated group, in this case phenyl, is either directly bound by a single covalent bond ($C_0$), or attached by an alkyl chain having the specified number of carbon atoms, in this case from 1 to about 4 carbon atoms. Examples of alkyl include, but are not limited to, methyl, ethyl, n-propyl, isopropyl, n-butyl, t-butyl, n-pentyl, and sec-pentyl. Preferred alkyl groups are lower alkyl groups, those alkyl groups having from 1 to about 8 carbon atoms, e.g. $C_1$-$C_8$ and $C_1$-$C_6$ alkyl groups.

The 1,2-aminoalcohol derivatives can have one or more chiral center. As a result, one may selectively prepare one optical isomer, including diastereomers and enantiomers, over another, for example by chiral starting materials, catalysts or solvents, or may prepare both stereoisomers or both optical isomers, including diastereomers and enantiomers at once (a racemic mixture). Since the compounds may exist as racemic mixtures, mixtures of optical isomers, including diastereomers and enantiomers, or stereoisomers may be separated using known methods, such as through the use of, for example, chiral salts and chiral chromatography.

In addition, it is recognized that one optical isomer, including a diastereomer and enantiomer, or a stereoisomer, may have favorable properties over the other. When a racemic mixture is discussed herein, it is clearly contemplated to include both optical isomers, including diastereomers and enantiomers, or one stereoisomer substantially free of the other.

Suitable compounds of Formula 1 include 2-amino-2-[2-(4-octaphenyl)ethyl]propane-1,3 diol also known as FTY720 (Formula II) and a derivative of FTY720 in which a hydroxymethylene substituent is replaced by a methyl group also known as AAL or 2-amino-2-methyl-4-[4-heptoxy-phenyl]butane-1-ol (Formula III).

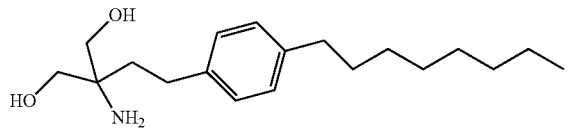

(II)

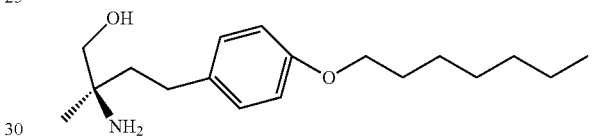

(III)

In vivo, FTY-720 and AAL can be phosphorylated by endogenous kinases such as, for example, the SK2 kinase, to produce compounds of formulas (IV) (FTY720-P or 2-amino-3-phosphate-2-[2-4-octaphenyl)ethyl]propane-1-ol) and (V) ((R)-AFD or 2-amino-2-methyl-4-[4-heptoxy-phenyl]1-diphosphoric acid), respectively.

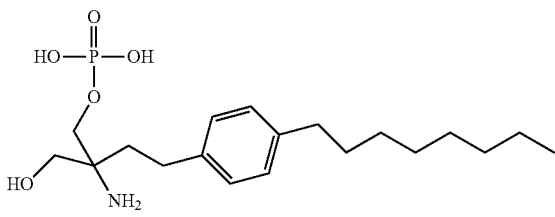

(IV)

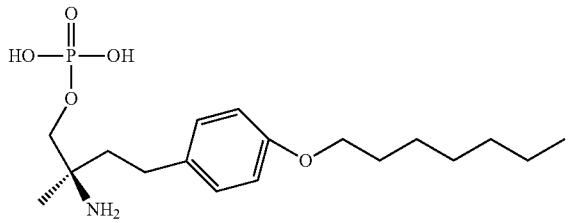

(V)

The vascular endothelial sphingosine-1-phosphate receptor agonist may be 2-amino-2-[2-(4-octaphenyl)ethyl]propane-1,3 diol; 2-amino-2-methyl-4-[4-heptoxy-phenyl]butane-1-ol; 2-amino-3-phosphate-2-[2-4-octaphenyl)ethyl]propane-1-ol; 2-amino-2-methyl-4-[4-heptoxy-phenyl]1-diphosphoric acid; or a combination comprising one or more of the foregoing agonists.

The agonist of a vascular endothelial S1P receptor may be administered to a mammal in an effective amount to treat a vascular permeability disorder. Such disorders include, for example, endothelial injury, thrombocytopenia, atherosclerosis, ischemic cardiovascular disease, ischemic peripheral vascular disease, peripheral vascular disorders associated with diabetes, Dengue hemorrhagic fever, adult (acute) respiratory distress syndrome, vascular leak syndrome, sepsis, autoimmune vasculitis, and combinations comprising one or more of the foregoing disorders.

Endothelial injury can be caused by hypertension, stress-induced hormones, chemical toxins, pollution, cholesterol, infectious agents (e.g., *Chlamydia pneumoniae, Helicobacter pylori*, herpesviruses, *Candida albicans*), homocysteine, and various diseases. Conditions related to endothelial injury include atherosclerosis and hemangioma. Atherosclerosis is associated with lipid deposition in the subendothelial space. Accumulation of lipid is made possible by locally enhanced vascular endothelial permeability. An atheroma is a necrotic mass at the center of an atherosclerotic lesion. A hemangioma is a benign tumor consisting of dilated blood vessels.

Thrombocytopenia is a disorder in which the number of platelets (a type of blood cell) is abnormally low, sometimes associated with abnormal bleeding. Adult idiopathic thrombocytopenic purpura (ITP) usually results from development of an antibody directed against a structural platelet antigen (an autoantibody). Other disorders producing thrombocytopenia similar to ITP include immune thrombocytopenias secondary to a collagen vascular disorder (e.g., SLE) or to lymphoproliferative disease. Heparin-induced thrombocytopenia results from the binding of heparin-antibody complexes to Fc receptors on the platelet surface membrane. In thrombocytopenia, endothelial injury, increased vascular permeability and tissue edema are prevalent.

Ischemic heart disease is a condition in which heart muscle is damaged or works inefficiently because of an absence or relative deficiency of its blood supply. It is most often caused by atherosclerosis, and includes angina pectoris, acute myocardial infarction, chronic ischemic heart disease and sudden death. It is also called coronary heart disease (CHD).

Several vascular permeability disorders are associated with Diabetes Mellitus including diabetic retinopathy, diabetic nephropathy, diabetic microvasculopathy, diabetic macrovasculopathy, and occlusive vascular disorder.

Dengue hemorrhagic fever is caused by one of four closely related, but antigenically distinct, virus serotypes (DEN-1, DEN-2, DEN-3, and DEN-4), of the genus *Flavivirus*. Infection with one of these serotypes does not provide cross-protective immunity, so an individual can have four dengue infections during their lifetimes. Dengue is a disease of the tropics, and the lifecycle of the viruses that cause it involves humans and *Aedes aegypti*, a domestic, day-biting mosquito that feeds on humans. The major pathophysiological abnormality seen in dengue hemorrhagic fever/dengue shock syndrome (DHF/DSS) is an acute increase in vascular permeability. Dengue is characterized by abrupt onset high fever, chills, headache, rash, signs of bleeding, changes in taste, sore throat, nausea, vomiting, diarrhea, and severe aching myalgia and arthralgia. In extreme cases, Dengue shock leads to leakage of plasma and subsequently to hypovolemic shock if the loss of plasma is critical.

Systemic vascular leak syndrome is a disorder characterized by recurrent episodes of hypotension and hemoconcentration due to sudden transient extravasation of 10% to 70% of plasma. Clinically, this syndrome presents with hypotension, hemoconcentration, and hypoalbuminemia. During quiescent periods, capillary permeability is normal. Extravasation occurs only during an episode. The pathophysiology of this leak remains enigmatic. Activation of classic pathway complement, persistent low-grade endogenous stimulation of 5-lipoxygenase, and a role for interleukin-2 have been suggested as possible causes.

Adult (acute) respiratory distress syndrome (ARDS) is the rapid onset of progressive malfunction of the lungs, especially the ability to take in oxygen, often associated with the malfunction of other organs. The condition is associated with extensive pulmonary inflammation and small blood vessel injury in the affected organs. The initial injury is to either the capillary endothelium or alveolar epithelium. There is increased capillary permeability followed by organization and scarring. The capillary defect is produced by an interaction of inflammatory cells and mediators such as leukocytes and cytokines that damage the endothelium and allows fluid and proteins to leak.

Sepsis is one condition which can lead to Systemic Inflammatory Response Syndrome (SIRS). Infections are typically local, however, an infection may be severe enough to cause overspill of active mediators into the blood stream from the local site of infection or infectious organisms may spread from this site to cause systemic infection or sepsis. About 50% of sepsis is caused by Gram negative organisms in which the major effector molecule is the lipopolysaccharide. Sepsis can result in increased vascular permeability and in extreme cases can result in multiple organ failure.

Autoimmune vasculitis is a group of diseases characterized by inflammation and damage to the blood vessels, thought to be brought on by an autoimmune response. Vasculitis-induced injury to blood vessels may lead to increased vascular permeability, vessel weakening that causes aneurysm formation or hemorrhage, and intimal proliferation and thrombosis that result in obstruction and local ischemia.

The invention also includes methods of treating unwanted vascular endothelial cell apoptosis such as an apoptosis-related disorder by administering an effective amount of an agonist of a vascular endothelial S1P receptor. The unwanted apoptosis is not related to transplant rejection. Apoptosis is a carefully controlled series of cellular events which ultimately leads to death of the cell. The morphological characteristics of apoptosis include cell shrinkage and loss of cell-cell contact, condensation of nuclear chromatin followed by fragmentation, the appearance of membrane ruffling, membrane blebbing, and apoptotic bodies. At the end of the process, neighboring cells and macrophages phagocytose the fragments from the apoptotic cell. The best-defined biochemical event of apoptosis involves the orderly destruction of nuclear DNA. Signals for apoptosis promote the activation of specific calcium- and magnesium-dependent endonucleases that cleave the double stranded DNA at linker regions between nucleosomes. This process results in the production of DNA fragments that are multiples of about 180 to about 200 base pair fragments Dysregulation of apoptosis can play an important role in disease states, and diseases can be caused by the occurrence of excessive or too little apoptosis. An example of a disease associated with too little apoptosis would be certain cancers. Examples of apoptosis-related diseases related to excessive or inappropriate apoptosis include ischemic disease (excluding reperfusion injury), peripheral thrombosis, neurodegenerative disease, peripheral nerve damage, aplastic anemia, liver damage, and HIV infection. In addition, endothelial apoptosis is a hallmark of radiation therapy which is used to treat tumors. S1P receptor agonists may be useful to treat patients undergoing radiation therapy to protect vascular function.

Apoptosis is a principal underlying cause of cell death in heart failure. Examples of the ischemic diseases include heart disease such as idiopathic cardiomyopathy, cardiomyopathy induced by drugs (e.g., adriamycin) or by chronic alcoholism, familial cardiomyopathy, viral myocarditis or cardiomyopathy, cardiac infarction, cardiac angina, congestive heart failure and arrhythmia, and cerebrovascular diseases such as cerebral stroke, subarachnoidal hemorrhage, cerebral infarction, and cerebral thrombosis.

Apoptosis is also related to several neurodegenerative diseases. Examples of such neurodegenerative diseases include Alzheimer's disease, Parkinson's disease, Huntington's disease, amyotrophic lateral sclerosis, and resinitis pigmentosa. Use of a vascular endothelial S1P receptor agonist may allow repair of vascular injury that induces neuronal damage.

The invention further includes methods of stimulating new blood vessel growth by administering an agonist of a vascular endothelial S1P receptor. New blood vessel formation can be stimulated in an organ-specific manner, for example, by expressing sphingosine kinase-2 in a given tissue by viral transduction and inducing local FTY720-P production by oral administration of FTY720. Such treatments may be used to treat the legs of diabetic individuals which can have defective blood vessel growth. An agonist of a vascular endothelial S1P receptor could be used to stimulate vessel growth in this situation. In addition, stimulating new blood vessel growth in the heart may be beneficial for cardiac function in individuals with heart disease. For example, sphingosine kinase-2 can be induced to be expressed in the heart by viral gene therapy, followed by FTY720 administration so that locally FTY720-P is produced and induces angiogenesis in the heart.

Daily dosages for administration of the vascular endothelial S1P receptor agonists will vary depending upon, for example, the agonist employed, the host, the mode of administration, and the severity of the condition to be treated. A suitable daily dosage is about 0.01 to about 10 milligrams per kilogram (mg/kg) per day, or about 0.1 to about 2.5 mg/kg per day, as a single dose or in divided doses. Suitable unit dosage forms for oral administration comprise about 1 to about 100 mg, or about 5 to about 50 mg active ingredient, e.g. FTY720, together with one or more pharmaceutically acceptable diluents or carriers. As an alternative, the agonist may be administered in free form or in pharmaceutically acceptable salt form may also be administered twice or three times a week, e.g. at a dosage as indicated above.

Pharmaceutical compositions comprising the vascular endothelial S1P receptor agonists may comprise additional pharmacological agents used in the treatment of disorders relating to vascular permeability and vascular endothelial cell apoptosis. Suitable additional pharmacological agents include, for example, cytotoxic agents, chemotherapeutic agents, hormones, steroidal anti-inflammatory drugs (e.g., prednisone, corticosteroids, and the like), non-steroidal anti-inflammatory drugs (e.g., NSAIDs, aspirin, acetaminophen, and the like); and combinations comprising one or more of the foregoing additional pharmacological agents.

Pharmaceutical compositions may be formulated using one or more physiologically acceptable carriers or excipients. Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by means known in the art with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); wetting agents (e.g., sodium lauryl sulfate); and combinations comprising one or more of the foregoing excipients. The tablets may be coated by methods well known in the art. Liquid preparations for oral administration may take the form of, for example, solutions, syrups, or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); preservatives (e.g., methyl or propyl-p-hydroxybenzoates or sorbic acid); and combinations comprising one or more of the foregoing additives. The preparations may also contain buffer salts, flavoring, coloring, and sweetening agents as appropriate.

Preparations for oral administration may be suitably formulated to give controlled release of the active compound. For buccal administration the compositions may take the form of tablets or lozenges formulated by techniques known in the art. For administration by inhalation, the compounds are conveniently delivered in the form of an aerosol spray presentation from pressurized packs or a nebuliser, with the use of a suitable propellant, for example, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the compound and a suitable powder base such as lactose or starch. The compounds may be formulated for parenteral administration by injection, for example, by bolus injection or continuous infusion. Formulations for injection may be presented in unit dosage form, for example, in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form for constitution with a suitable vehicle, for example, sterile pyrogen-free water, before use. The compounds may also be formulated in rectal compositions such as suppositories or retention enemas, for example, containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Because the SK2 kinase phosphorylates FTY720 in vitro and in vivo, measurement of an individual's level of the SK2 kinase may be used to predict the effectiveness of a vascular endothelial S1P receptor agonist in the treatment of disease. For example, this test may be used to predict if a given individual is a candidate for FTY720 therapy. Alternatively, if an individual has a low level of SK2 kinase, preferred compounds for administration may be a phosphorylated form of a vascular endothelial S1P receptor agonist or another S1P receptor agonist with a different chemical structure.

The invention is further illustrated by the following non-limiting examples.

EXAMPLES

General Methods

Reagents. Fatty acid-free serum albumin (ffa-BSA), 4-deoxypyridoxine and β-glycerophosphate, fluorescein isothiocyanate (FITC)-dextran (average MW=2,000 kilodaltons (kDa) and 165 kDa) were purchased from Sigma Chemical Co. Sphingosine, N,N-dimethylsphingosine (DMS) and S1P were purchased from Biomol Research Laboratories, Inc. (Plymouth Meeting, Pa.). {$\gamma$-$^{32}$P}ATP (specific activity 6,000 Ci/mmol) and {methyl-$^3$H}-thymidine (specific activity 86 Ci/mmol) were from Amersham. FTY720, phospho FTY720, (S)-AAL, (R)-AAL and phospho-(R)-AAL were provided by Dr. V. Brinkmann, Novartis. Phospho-Akt, Akt, phospho-ERK1/2 and ERK-1/2 antibodies were from Cell Signaling Tech., and VE-cadherin antibody was from Santa Cruz Biotech.

cDNA cloning of murine SK1 and SK2. Mouse liver RNA (Ambion) was used to amplify the murine spingosine kinase (SK1 and SK2) cDNA by reverse transcription-PCR with the forward primers SEQ ID NO:1 (AGC CCC ATG TGG TGG TGT TGT) and SEQ ID NO:2 (ATT ATG GCC CCA CCA CCA CTA CT), respectively and reverse primers SEQ ID NO:3 (GGC ACA GAG TTA TGG TTC TTC) and SEQ ID NO:4 (AGG TCA GGC TTG TGG CTT TTG AC), respectively. The resulting PCR product was cloned in pcDNA3.1 Topo vector (Invitrogen), and the DNA sequence was confirmed. SK1 and SK2 cDNAs were then cloned in pcDNA3.1 eukaryotic expression vector (Invitrogen).

Cell culture and transfection. HUVEC (Clonetics, p4-11) were cultured in M199 medium supplemented with 10% fetal bovine serum (FBS) and heparin-stabilized endothelial cell growth factor. 293T cells in 60 mm dishes were transfected with four micrograms ($\mu$g) of vector alone or with vectors containing SK constructs by the calcium phosphate method. 24 hours after transfection, cells were harvested by scraping at 4° C. with 400 microliters ($\mu$l) of 25 millimolar (mM) HEPES pH 7.5, 5 mM MgCl$_2$, 1× protease inhibitor mixture (Calbiochem), and disrupted by brief sonication. Cellular homogenates were centrifuged for 10 minutes, 4° C. at 20,000×g.

Statistical analysis. All experiments were performed two to five times, and a representative experiment is shown. In migration and apoptosis experiments, results represent mean values of triplicates. P values were calculated by Student's t test using Microsoft Excel software.

Example 1

Phosphorylation of FTY720 by Sphingosine Kinases in Vascular Endothelial Cells

Since S1P is a potent inducer of endothelial cell chemotaxis, the effect of FTY720 and its analogues on endothelial cell migration was tested. HUVEC migration was assayed using a 96 well chemotaxis microchamber (Neuro Probe, Inc.) (Paik, J. H. et al. *J Biol Chem* 276:11830-11837 (2001)). Briefly, polycarbonate filters with a pore size of 8 micrometers ($\mu$m) were coated with five micrograms per milliliter ($\mu$g/ml) fibronectin. S1P, FTY720, AAL, FTY720-P or (R)-AFD were diluted in 0.1% ffa-BSA into the appropriate concentration. 85 $\mu$l of the solutions or conditioned medium from HUVEC were added into the lower chamber. Approximately 5×10$^4$ cells suspended in M199 with 0.1% bovine serum albumin were placed in the upper compartment. The cells were allowed to migrate for 4 hours at 37° C. in a humidified chamber with 5% CO$_2$. After the incubation period, the filter was removed, and cells were stained in 0.1% crystal violet and eluted with 10% acetic acid in 96-well plates. Quantification was done based on absorbance at 575 nanometers (nm) by a Spectramax 340 (Molecular Devices) plate reader.

Activation of FTY720 and (R)-AAL by endothelial cells was performed by washing cells three times with plain medium M199 and incubating with 0.1% fatty acid free BSA containing different concentrations of FTY720 or (R)-AAL for three hours. After incubation, conditioned medium was removed, centrifuged at 1,000×g for 10 minutes, and used in the migration assay.

FIG. 1 shows the results of a migration experiment with HUVECs (white bars: control, black bars: *Pertussis* toxin treatment) using the following chemoattractants: S1P (100 nanomolar (nM)), variable concentrations of FTY720 (FTY) and AAL, conditioned medium from endothelial cells after a 3 hour incubation with the indicated concentrations of FTY720 (FTY), (R)-AAL or (S)-AAL. Data=mean±SE of triplicate values from a representative experiment repeated three times (N=3). *p<0.01 vs. vehicle control, # p<0.01 vs. cells without *Pertussis* toxin.

Neither FTY720 nor its structural analog (R)-AAL induced endothelial cell migration in a wide concentration range (FIG. 1). However, when FTY720 or (R)-AAL was incubated with HUVEC for 3 hours, they were activated into potent chemoattractants for endothelial cells. This conditioned medium-induced migration was dose-dependent and *Pertussis* toxin sensitive, indicating the involvement of a G$_i$-coupled receptor. In contrast, the enantiomer (S)-AAL, which cannot be phosphorylated by sphingosine kinase (SK), did not induce migration after incubation with endothelial cells. These data are consistent with the hypothesis that endothelial cells phosphorylate and activate FTY720 and (R)-AAL into the phosphorylated derivatives, which are chemoattractants for endothelial cells. The presence of the SK1 and SK2 transcripts was detected in HUVEC cells by RT-PCR using primers SEQ ID NOs:1-4; TGGAGTATGAATGCCCCTAC, CGCTAACCATCAATTCCCC, for SK1 and GATCAC-CCCTGACCTGCTAC, GGCATCTTCACAGCTTCCTC for SK2 (data not shown).

Figure 2:
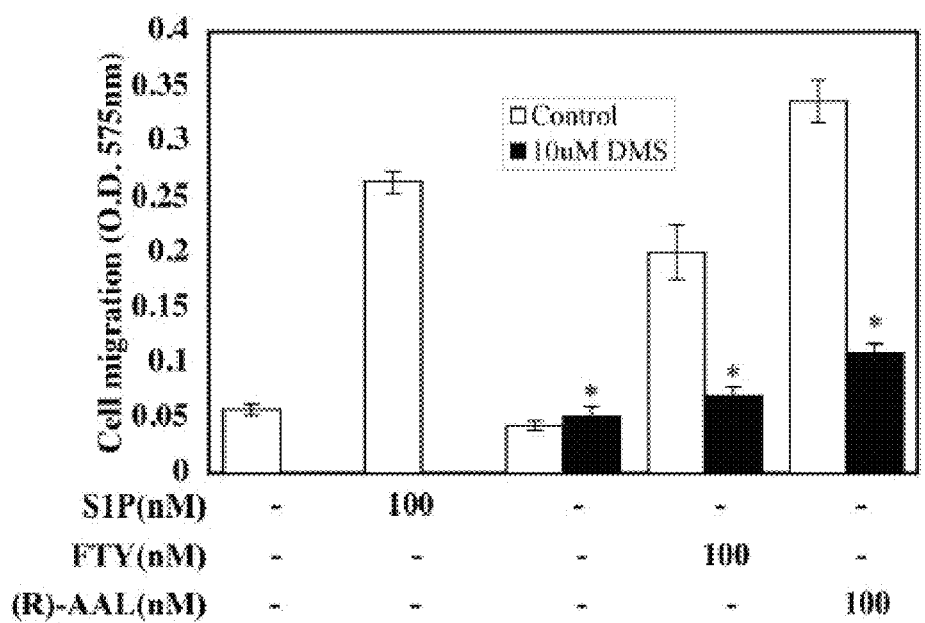
FIG. 2 is a graph of the results of a cell migration assay demonstrating that the ability of endothelial cells to activate FTY720 and (R)-AAL is blocked by the sphingosine kinase (SK) inhibitor dimethylsphingosine (DMS).

In order to further explore the possibility that SK1 and SK2 are involved in FTY720 phosphorylation, DMS, a SK inhibitor, was tested for blockage of conversion of FTY720 and (R)-AAL into active forms. FIG. 2 shows the results of a migration experiment with HUVECs using: S1P (100 nM) or conditioned medium from endothelial cells after 3 hour incubation with 100 nM FTY720 (FTY) or 100 nM (R)-AAL in the absence (white bars) or presence (black bars) of 10 $\mu$M DMS. *p<0.01, DMS vs. vehicle control. DMS treatment (10 $\mu$M) potently inhibited the ability of endothelial cells to activate FTY720 and (R)-AAL (FIG. 2). These results suggest that SK activity present in HUVEC was able to phosphorylate and activate both FTY720 and (R)-AAL.

Example 2

Confirmation of phosphorylation of FTY720 and R-AAL

To confirm that FTY720 and (R)-AAL are phosphorylated by endothelial cells, an in vitro kinase assay was performed with both total cell extract and conditioned medium from HUVEC. Cells were washed three times with plain medium M199 and incubated with 0.1% ffa-BSA for the times indicated. After incubation, conditioned medium was removed, centrifuged at 1,000×g for 10 minutes, and used for the kinase activity assay. Cells were scraped at 4° C. with 400 $\mu$l of 25 mM HEPES pH 7.5, 5 mM MgCl$_2$, 1× protease inhibitor mixture, and disrupted by brief sonication. Cellular homogenates were centrifuged for 10 minutes, 4° C. at 20,000×g. In the kinase assay, 300 $\mu$l of conditioned medium (derived from 5×10$^5$ cells for 3 hours of incubation) or 10 $\mu$g of total cell extract from HUVEC were used as a source of kinase activity. Reactions contained 20 $\mu$M sphingosine or 100 $\mu$M FTY720 or AAL, [$\gamma$-$^{32}$P]ATP (10 $\mu$Ci), 5 mM MgCl$_2$, 15 mM NaF, 0.5 mM 4-deoxypyridoxine, 40 mM-glycerophosphate and 300 $\mu$l of M199 and were incubated at 37° C. for 30 minutes. Lipids were extracted and samples were resuspended in 50 $\mu$l of chloroform. Lipids were resolved by TLC on Silica Gel G60 using 1-butanol/acetic acid/water (60/20/20 volume/volume) buffer and quantified with a PhosphorImager (Molecular Dynamics).

Figure 3:
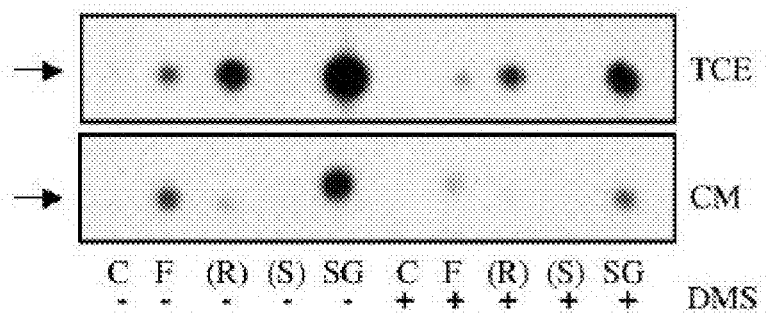
FIG. 3 is thin layer chromatography (TLC)-autoradiography from an in vitro kinase assay with conditioned medium (CM) and total cell extract (TCE) from HUVECs.

As shown in FIG. 3, FTY720 and (R)-AAL were phosphorylated by the kinase activity present in HUVEC (FIG. 3 top panel, specific activity 3.85±0.75 and 15±0.93 picomol per milligram per minute, respectively). As predicted, sphingosine was an efficient substrate for this kinase activity (specific activity 75.7±6 (picomoles per milligram per minute (pmol/mg/min)). In contrast, (S)-AAL phosphorylation was undetectable, in agreement with the results obtained with the migration assay. Phosphorylation of both FTY720 and (R)-AAL was inhibited by DMS (50 µM). Similarly, kinase activity was detected in the conditioned medium from HUVECs (FIG. 3, bottom panel) and was inhibited by Triton X-100 and increased by KCl (200 mM) (data not shown), which are conditions that favor the enzymatic activity of SK.

Example 3

Confirmation of the Role of SK2 in FTY720 and (R)-AAL Phosphorylation

Figure 4:
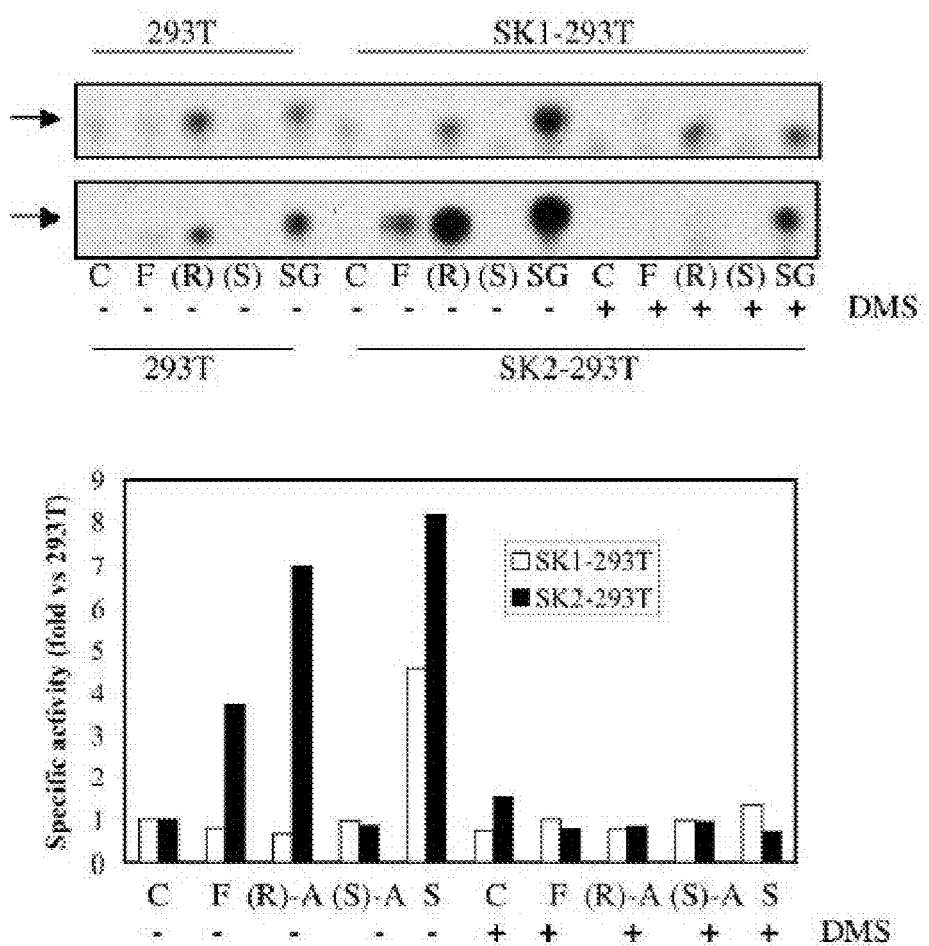
FIG. 4 is TLC-autoradiography from an in vitro kinase assay conducted with extracts from Vector control 293T cells (293T), SK1 overexpressing 293T cells (SK1-293T) and SK2 overexpressing 293T cells (SK2-293T). The fold induction of specific activity of SK1-293T (white bars) and SK2-293T (black bars) vs. vector transfected 293T is shown in the bottom panel.

In order to confirm the role of SK2 in FTY720 and (R)-AAL phosphorylation, HEK293T cells were transiently transfected with a pcDNA3.1/Neo expression vector containing either SK1 or SK2 cDNA, and checked for FTY720, (R)-AAL and (S)-AAL phosphorylation. FIG. 4 shows TLC-autoradiography from an in vitro kinase assay conducted with extracts from Vector control 293T cells (293T), SK1 overexpressing 293T cells (SK1-293T) and SK2 overexpressing 293T cells (SK2-293T). Vehicle control=(C), 100 µM FTY720=(F), 100 µM (R)-AAL=(R), 100 µM (S)-AAL=(S) or 20 µM sphingosine=(SG) are used as substrates. 50 µM DMS was included when indicated (+). A representative experiment of N=3-5 is shown. The fold induction of specific activity of SK1-293T (white bars) and SK2-293T (black bars) vs. vector transfected 293T is shown in the bottom panel. Arrows indicate the phosphorylated compound.

Modest levels of endogenous sphingosine kinase activity were detected in vector-transfected cells (FIG. 4). SK1 cell extracts presented FTY720 or (R)-AAL kinase activity similar to control 293T cells while sphingosine phosphorylation was significantly increased in SK1-293T cells (specific activity 48.1 pmol/mg/min vs. 10.5 in 293T, FIG. 4). However SK2-293T cells showed an increased FTY720 and (R)-AAL kinase activity versus control 293T cells (3.7 and 7-fold induction, respectively). The specific activity in SK2-293T was 41.6, 199.5 and 319.9 pmol/min/mg for FTY720, (R)-AAL and sphingosine, respectively. (S)-AAL phosphorylation by 293T, SK1-293T and SK2-293T cells was barely detectable. FTY720, (R)-AAL and sphingosine kinase activity was blocked by incubation with DMS (50 µM). These results suggest a role for SK2 in FTY720 and (R)-AAL phosphorylation, and thus, in the activation of these compounds into S1P receptor agonists. Moreover, the results indicate that HUVEC were able to phosphorylate and activate both FTY720 and (R)-AAL present in the extracellular medium.

Example 4

Effects of FTY720-P on Endothelial Cell Responses

Figure 5:
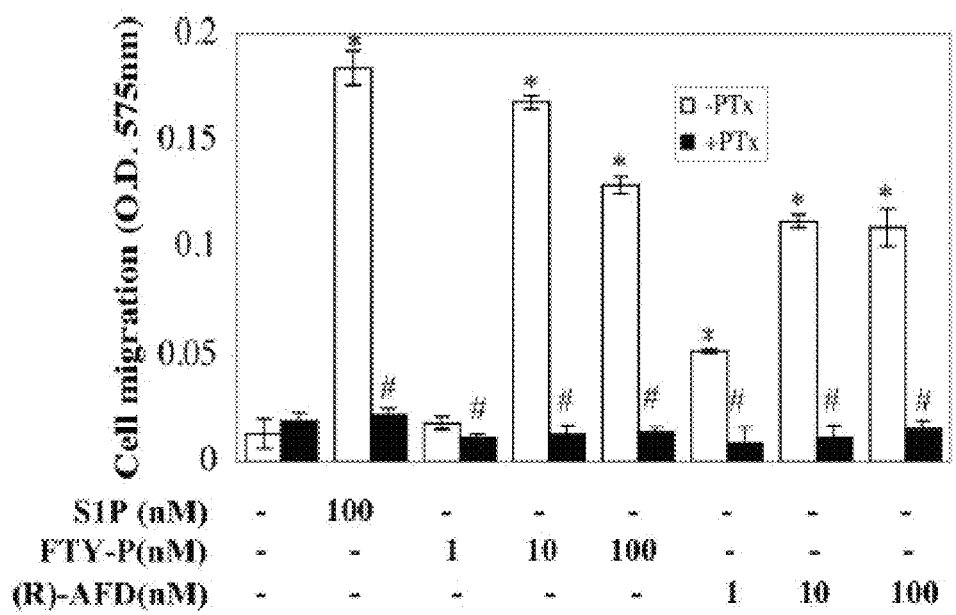
FIG. 5 is a migration experiment with HUVECs (white bars: control, black bars: *Pertussis* toxin treatments) using: S1P (100 nM), FTY720-P (FTY720-P) or (R)-AFD (the phosphorylated form of (R)-AAL) at the indicated concentrations.

The effects of FTY720-P and its analog (R)-AFD were studied in HUVEC. In FIG. 5, Data=mean±SE of triplicates. N=3. *p<0.01, treatments vs. vehicle control, # p<0.01 vs. cells without Pertussis toxin. Both FTY720-P and (R)-AFD were potent chemoattractants for HUVEC (FIG. 5). Both had their maximum effect at 10 nM (13 and 9-fold induction, respectively), although S1P was slightly more potent (14-fold induction). FTY720-P and (R)-AFD-induced migration was blocked by Pertussis toxin (200 ng/mL), indicating that it is an effect mediated by the heterotrimeric $G_i$ protein pathway.

Endothelial cell morphogenesis, a phenomenon that requires endothelial cell migration, survival and adherens junction assembly, is mediated by the ligand-dependent activation of $S1P_1$ and $S1P_3$ receptors. S1P has been shown to induce Akt protein kinase and ERK protein kinase phosphorylation in endothelial cells, and Akt-mediated phosphorylation of $S1P_1$/EDG-1 receptor is required for S1P-induced migration. The effects of FTY720-P and analogs on Akt and ERK phosphorylation in HUVEC were studied in a Western blot analysis. Confluent cultures of HUVEC cells were serum starved for two hours in 0.1% ffa-BSA M199 before treatments. Then, they were washed with ice-cold phosphate buffered saline (PBS) containing 1 mM sodium fluoride and 1 mM sodium orthovanadate and homogenized in radioimmunoprecipitation assay buffer (0.1% sodium dodecyl sulfate (SDS), 0.5% sodium deoxycholate, 1% NP-40, 1 mM sodium orthovanadate, 50 mM β-glycerophosphate and 1× protease inhibitor cocktail). Samples were centrifuged 10,000×g for 10 minutes, and protein concentrations of supernatants were determined by Bradford assay (BioRad Protein Dye Reagent). Equal amounts of protein were separated on a 10% polyacrylamide gel and blotted to a nitrocellulose membrane. Immunoblot analysis was performed using Phospho-Akt, Akt, phospho-ERK1/2 or ERK-1/2 antibodies.

Figure 6:
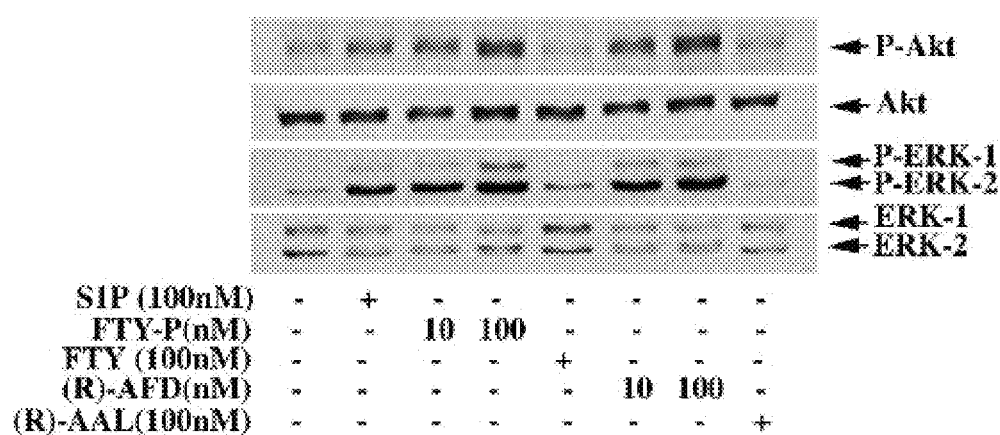
FIG. 6 shows a Western blot of phospho-Akt, total Akt, phospho-ERK-1/2 and total ERK-1/2 levels in HUVEC after 5 minute stimulation with S1P, FTY720-P (FTY720-P), FTY720 (FTY), (R)-AFD or (R)-AAL at the indicated concentrations.
Figure 7:
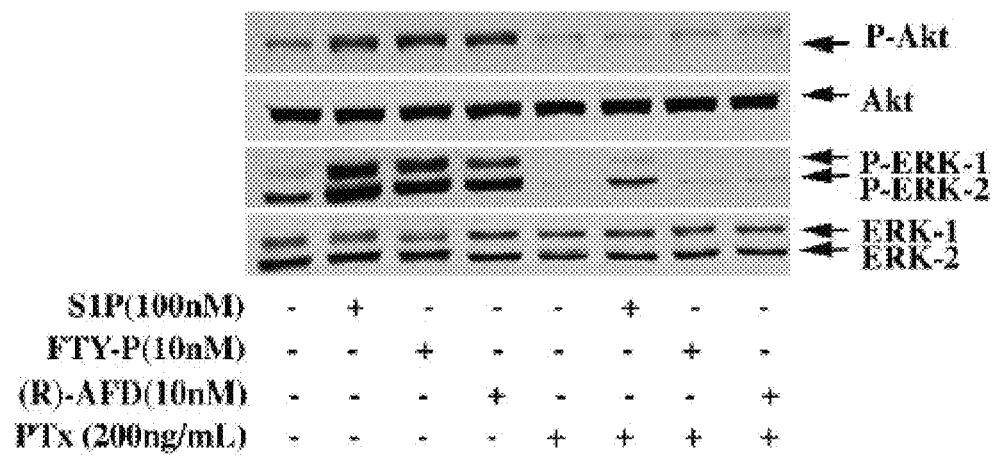
FIG. 7 shows a Western blot demonstrating that *Pertussis* toxin treatment prevents Akt and ERK-1/2 phosphorylation by S1P, FTY720-P (FTY720-P) and (R)-AFD.

Both FTY720-P and (R)-AFD induced an increase in Akt (3.7 and 4.5 fold at 100 nM, respectively, FIG. 6) and ERK-1/2 (9.3 and 8.2 fold at 100 nM, respectively FIG. 6) phosphorylation levels after 5 minutes. The time course of this phosphorylation was similar for FTY720-P, (R)-AFD and S1P, being the maximum phosphorylation levels achieved after a 5 minute stimulation (data not shown). The effect of FTY720-P and (R)-AFD on Akt and ERK phosphorylation was dose-dependent (data not shown) and the extent of the phosphorylation induced by FTY720-P and (R)-AFD was higher than the one induced by S1P. However, the non-phosphorylated derivatives, FTY720 or AAL, did not induce phospho-Akt or phospho-ERK-1/2 levels in endothelial cells. Akt and ERK-1 and ERK-2 phosphorylation by S1P, FTY720-P and (R)-AFD was blocked by incubation with Pertussis toxin (FIG. 7), indicating the involvement of a $G_i$-coupled receptor.

Example 5

Effect of FTY720-P and (R)-AFD on Apoptosis

Since ERK-1 and ERK-2 activation is necessary for the survival effect of S1P in endothelial cells, it was tested if FTY720-P and its analog (R)-AFD could prevent apoptosis induced by serum deprivation in HUVEC. In this test, HUVEC cells were labeled with {methyl-$^3$H}-thymidine (1 µCi/ml) for 16 hours. Then, they were washed and 0.1% ffa-BSA M199 containing the different treatments was added. After 8 hours, fragmented DNA was solubilized and quantified as described.

Figure 8:
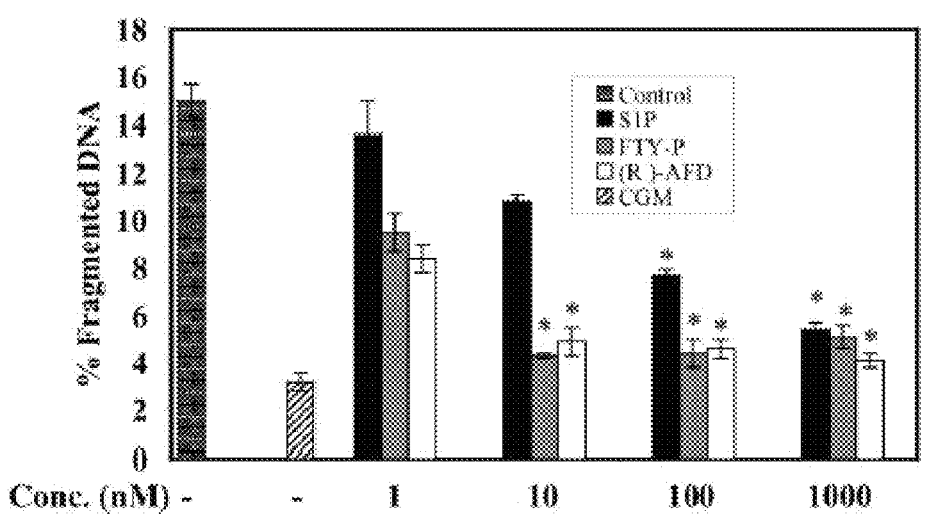
FIG. 8 shows a study of the effects of FTY720-P on apoptosis by measuring the percentage of DNA fragmentation after {methyl-$^3$H}-thymidine incorporation in HUVEC cells.
Figure 9:
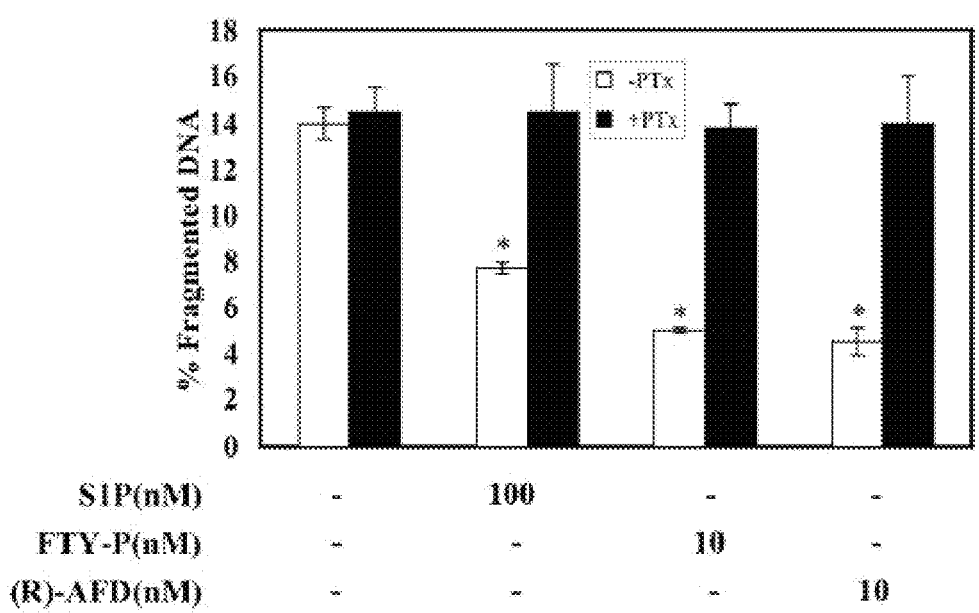
FIG. 9 is a DNA fragmentation assay showing that *Pertussis* toxin treatment abolishes the protective effect of S1P, FTY720-P and (R)-AFD on apoptosis.

The results are shown in FIGS. 8 and 9. FTY720-P and (R)-AFD significantly protected cells from apoptosis in a dose-dependent manner (FIG. 8), with a maximum effect at extremely low concentrations—10 nM (~70% inhibition of DNA fragmentation). A similar inhibition of DNA fragmentation was observed with S1P treatment but at a higher concentration (1 µM). The anti-apoptotic effects of S1P, FTY720-P and (R)-AFD were also blocked by Pertussis toxin treatment (FIG. 9), indicating that the signaling trough $G_i$ was crucial.

Example 6

FTY720-P Modulates Adherens Junction Assembly and Vascular Permeability In Vitro The effect of FTY720-P and (R)-AFD on VE-cadherin assembly, which is required to form adherens junctions, critical subcellular structures in endothelial cell morphogenesis and permeability, was evaluated. Cadherins are a family of cell adhesion molecules that are involved in the formation of specific cell-cell contacts. VE-cadherin (or cadherin-5) has been shown to be localized at intercellular junctions (adherens junctions) in cell-to-cell contacts. A number of experimental observations suggest that this cadherin is involved in various aspects of vascular biology related to angiogenesis, including the assembly of endothelial cells into tubular structures.

The effects of FTY720-P and (R)-AFD on the localization of VE-cadherin were studied using immunofluoroescence analysis. In this study, $2 \times 10^5$ cells were plated in 35 millimeter glass bottom petri dishes. Three days later, the cells were washed and serum starved for 3 hours before treatments. Then, the cells were washed with ice-cold PBS, fixed, and immunofluorescence analysis with VE-cadherin antibody was conducted (1 µg/ml Santa Cruz). The primary antibody staining was visualized with Rhodamine-conjugated goat anti-mouse (1:1000, Cappel) IgG. Confocal microscopy was conducted on a Zeiss LSM 510 laser-scanning confocal microscope. Rhodamine fluorescence was excited using a 543 nm Helium/Neon laser and emitted fluorescence was detected with a 530 nm long-pass filter.

Figure 10:
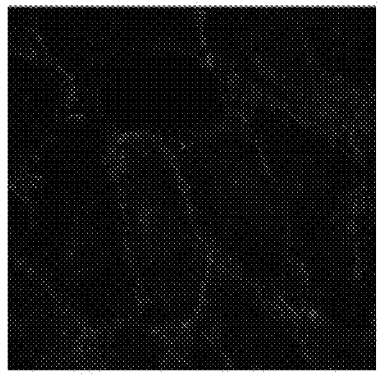
FIG. 10 is an immunofluorescence assay in which C: vehicle control, S1P: 100 nM S1P, FTY: 10 nM FTY720, FTY720-P: 10 nM FTY720-P, AAL: 10 nM (R)-AAL, AFD: 10 nM (R)-AFD. Scale bar=50 μm.
Figure 10:
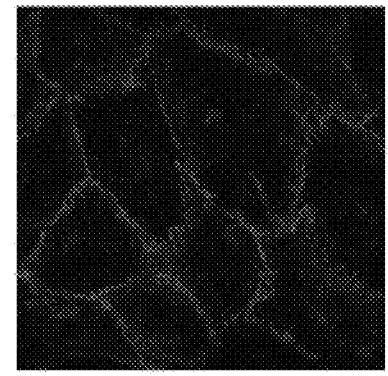
Figure 10:
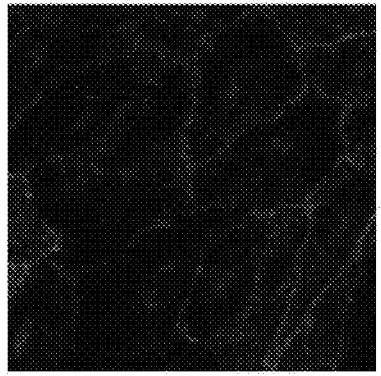
Figure 10:
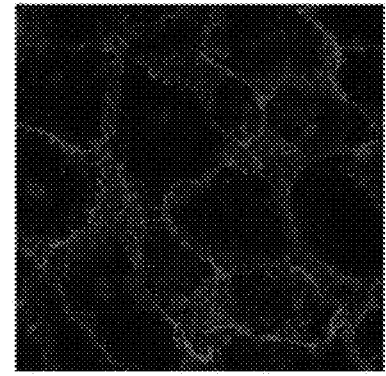
Figure 10:
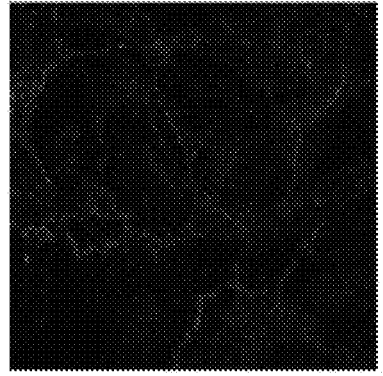
Figure 10:
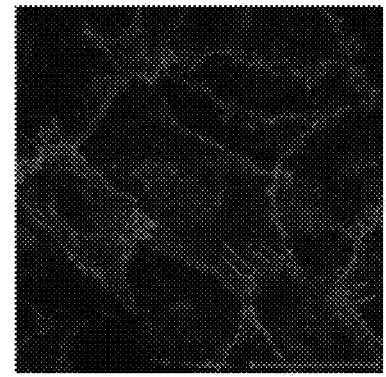

Treatment of HUVEC with FTY720-P and (R)-AFD for 30 minutes resulted in an increase in VE-cadherin localization at the cell-cell contact regions (FIG. 10). This effect was comparable to that observed for S1P. However, the non-phosphorylated precursors FTY and (R)-AAL did not induce VE-cadherin translocation to the adherens junctions. These results indicate that FTY720-P and (R)-AFD act on vascular S1P receptors to induce adherens junction assembly in endothelial cells.

Several studies have shown that VE-cadherin could be an important determinant of vascular permeability. VEGF-induced tyrosine phosphorylation of VE-cadherin resulted in increased vascular permeability in vitro. In addition, S1P was shown to inhibit thrombin induced paracellular permeability via a $S1P_1/G_i/Rac$ dependent process. A cellular system was used to assess the effects of S1P, FTY720-P and (R)-AFD on vascular permeability. Mouse embryonic endothelial cells ($5 \times 10^4$) were cultured for 2 days in Transwell polycarbonate filters (6.5 mm diameter, 0.4 µm pores; Costar). Culture medium was replaced with serum/phenol red-free DMEM (HEPES buffer, L-glutamine, and pyridoxine hydrochloride) (0.1 mL upper chamber and 0.6 mL lower chamber). Cells were pretreated with FTY720, derivatives or S1P for 1 hr. FITC-dextran (average MW=2,000 kDa), was added to the upper compartment either in the absence or presence of murine recombinant VEGF (50 ng/ml). Media from lower wells were taken after indicated time periods (5-45 minutes). Samples were placed in black solid bottom 96 well plates (Costar) and fluorescence intensities were measured using CytoFluor(R) fluorescence multi-well plate reader (Applied Biosystems) at 488 nm excitation. Data=mean±SE of duplicates. N=2. *$p<0.01$ VEGF vs. untreated. # $p<0.01$ treatments+VEGF vs. VEGF alone.

Figure 11:
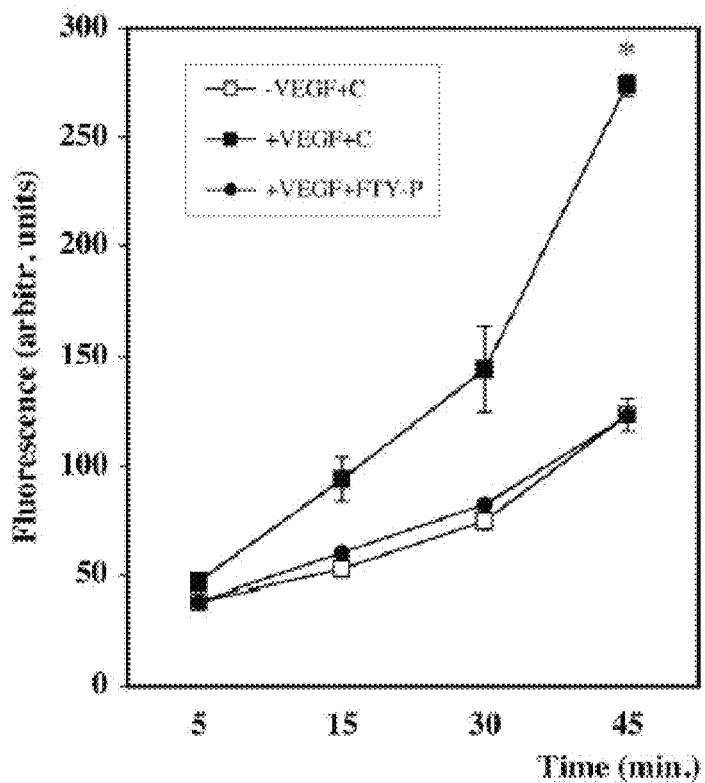
FIG. 11 is a graph of the time course of VEGF-induced paracellular permeability: VEGF:20 ng/mL, FTY720-P: 100 nM FTY720-P.
Figure 12:
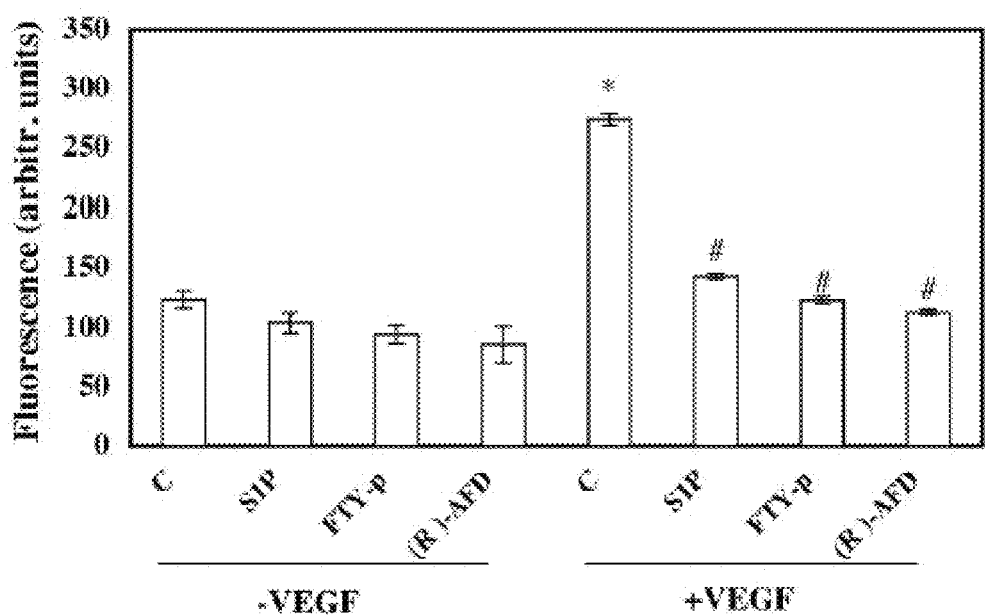
FIG. 12 is a graph demonstrating that 100 nM S1P (S1P), 100 nM FTY720-P (FTY720-P) and 100 nM (R)-AFD ((R)-AFD) inhibit VEGF-induced paracellular permeability.

The results of the paracellular permeability assay are shown in FIGS. 11 and 12. Without VEGF the fluorescence in the lower compartment increased over time (FIG. 11). However, when the cells were treated with VEGF, a significant increase in the fluorescence in the lower compartment was observed, which was profoundly inhibited by S1P, FTY720-P and (R)-AFD (FIG. 12, 45 minute time point is shown). These results indicate that VEGF-induced paracellular permeability is antagonized by the S1P receptor agonists S1P, FTY720-P and (R)-AFD.

Example 6

FTY720-P Modulates Adherens Junction Assembly and Vascular Permeability In Vivo The role of plasma borne FTY720-P or (R)-AFD in the regulation of vascular permeability was tested in vivo. In order to test this possibility, an in vivo vascular permeability model was used in FTY720, (R)-AFD or (S)-AAL-pretreated mice. Normal FVB/N female or male mice were treated by gavage with FTY720 (50 µg), S-AAL enantiomer (50 ng), R-AAL enantiomer (50 µg) and water as vehicle control. Five hours post-gavage, animals were anesthetized with 2% Avertin™ (0.5 cc/20 g) and infused through the tail vein with 100 µl FITC-dextran (5 mg/ml, 165 kDa) Animals were placed on a warming table under a fluorescent dissecting microscope (Zeiss STV11, Zeiss, Inc.) and the central vessels in the ear were imaged. Control saline or mouse vascular endothelial growth factor (mVEGF, 10 ng/ml) was injected subdermally into the middle ear using a 30 gauge needle (30 µl). Ear vasculature was then imaged with fixed exposure times in a stationary position from 5 minutes to 120 minutes post-injection. Fluorescence images were then quantified using pixel-based threshold in ImageProPlus (Media Cybernetics, Inc.) and quantified.

Figure 13:
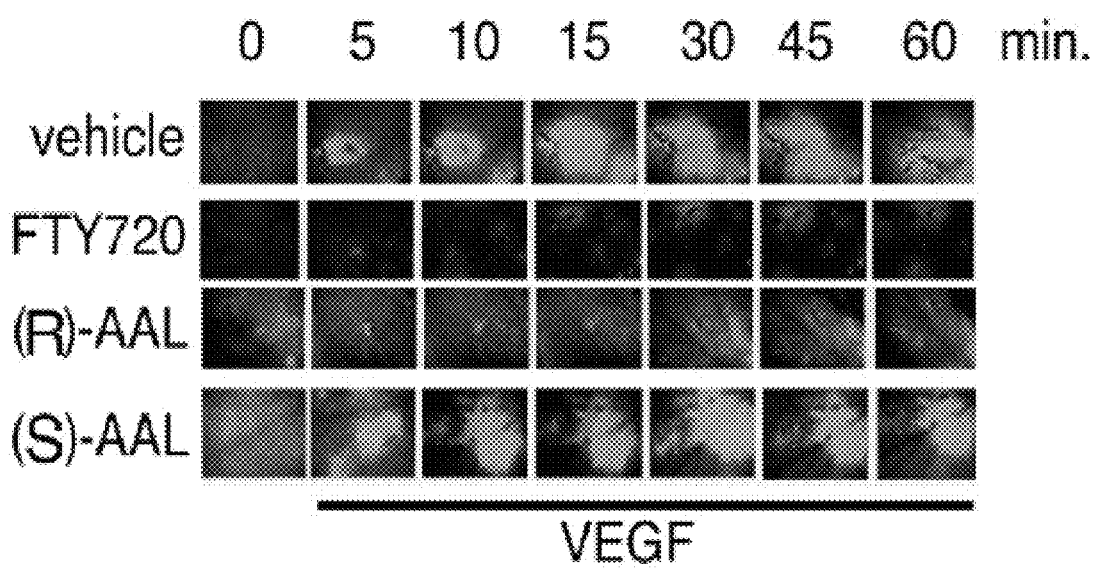
FIG. 13 shows fluorescence images of a mouse ear microvascular permeability assay.
Figure 14:
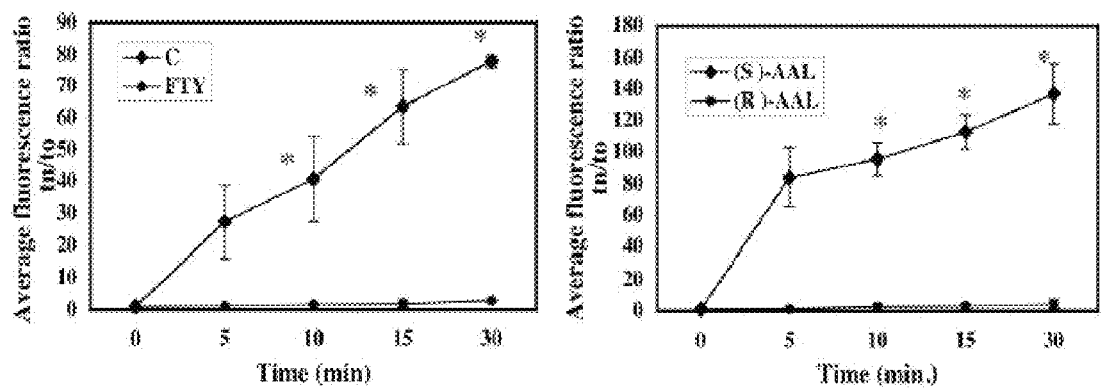
FIG. 14 shows quantification of extravascular fluorescence in the ear.

The results are shown in FIGS. 13 and 14. Pretreatment of the mice with a single oral administration 5 hours prior to the analysis showed that FTY720 profoundly suppressed vascular permeability induced by VEGF (FIGS. 13 and 14). (R)-AAL but not (S)-AAL also potently inhibited vascular permeability in vivo. These data suggest that phosphorylation of FTY-720 and (R)-AAL by sphingosine kinase in vivo and activation of S1P receptors on endothelial cells results in the inhibition of VEGF-induced vascular permeability.

Agonists of vascular endothelial S1P receptors have been shown to have effects on vascular permeability, apoptosis and angiogenesis. In particular, FTY 720 and its analogs have been shown to be phosphorylated in vivo to forms (e.g., FTY720-P) capable of binding vascular endothelial S1P receptors. Vascular endothelial S1P receptor agonists can be employed in the treatment of vascular permeability disorders, disorders related to excessive vascular endothelial apoptosis, and to grow new blood vessels.

All cited patents, patent applications, and other references are incorporated herein by reference in their entirety.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of treating Alzheimer's disease, comprising administering to a mammal in need of treatment for Alzheimer's disease a therapeutically effective amount of a compound selected from the group consisting of 2-amino-2-[2-(4-octylphenyl)ethyl]propane-1,3-diol, 2-amino-3-phosphate-2-[2-(4-octylphenyl)ethyl]propane-1-ol, or pharmaceutically acceptable salts thereof.

* * * * *